(12) United States Patent
Katsuki et al.

(10) Patent No.: US 10,888,224 B2
(45) Date of Patent: Jan. 12, 2021

(54) ESTIMATION MODEL FOR MOTION INTENSITY

(71) Applicant: INTERNATIONAL BUSINESS MACHINES CORPORATION, Armonk, NY (US)

(72) Inventors: Takayuki Katsuki, Tokyo (JP); Tetsuro Morimura, Tokyo (JP)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 16/032,731

(22) Filed: Jul. 11, 2018

(65) Prior Publication Data
US 2020/0015683 A1  Jan. 16, 2020

(51) Int. Cl.
| A61B 5/00 | (2006.01) |
| A61B 5/11 | (2006.01) |
| A61B 5/113 | (2006.01) |
| A61B 5/024 | (2006.01) |
| A61B 5/0205 | (2006.01) |

(52) U.S. Cl.
CPC .......... *A61B 5/0024* (2013.01); *A61B 5/0006* (2013.01); *A61B 5/113* (2013.01); *A61B 5/1114* (2013.01); *A61B 5/4815* (2013.01); *A61B 5/6891* (2013.01); *A61B 5/002* (2013.01); *A61B 5/0205* (2013.01); *A61B 5/02405* (2013.01); *A61B 5/4094* (2013.01); *A61B 5/4812* (2013.01); *A61B 5/4818* (2013.01); *A61B 2562/0219* (2013.01); *A61B 2562/0247* (2013.01)

(58) Field of Classification Search
CPC ... A61B 5/0024; A61B 5/0006; A61B 5/1114; A61B 5/113; A61B 5/4815
See application file for complete search history.

(56) References Cited

U.S. PATENT DOCUMENTS

| 2006/0042409 | A1* | 3/2006 | Nemoto ................ A61B 5/1115 73/866.1 |
| 2011/0034811 | A1* | 2/2011 | Naujokat ............ A61B 5/0245 600/484 |
| 2011/0068935 | A1* | 3/2011 | Riley ................. A61B 5/02055 340/575 |
| 2015/0164411 | A1* | 6/2015 | Selvaraj ............... A61B 5/1121 600/301 |
| 2015/0242608 | A1* | 8/2015 | Kim ..................... G06F 1/3231 726/19 |
| 2016/0314672 | A1* | 10/2016 | Wiggermann ..... G08B 21/0446 |
| 2017/0020432 | A1 | 1/2017 | Kusukame et al. |
| 2017/0143565 | A1* | 5/2017 | Childs .................... A61G 7/018 |
| 2018/0289310 | A1* | 10/2018 | Girouard .............. A61B 5/7267 |

FOREIGN PATENT DOCUMENTS

WO   2008096307 A1   8/2008

* cited by examiner

*Primary Examiner* — Amine Benlagsir
(74) *Attorney, Agent, or Firm* — Tutunjian & Bitetto, P.C.; Randall Bluestone (57) ABSTRACT

A computer-implemented method for learning a model to predict movements of a person in bed is presented. The method includes receiving first data from a plurality of first sensors installed on a bed patient support apparatus, receiving second data from a plurality of second sensors installed on the person, and learning a model to predict the second data based on the first data by assuming a sensing range of motion intensity by the plurality of first sensors is greater than a sensing range of motion intensity by the plurality of second sensors.

14 Claims, 7 Drawing Sheets

ESTIMATION MODEL FOR MOTION INTENSITY

BACKGROUND

Technical Field

The present invention relates generally to patient movement monitoring systems, and more specifically, to an estimation model for motion intensity of a patient in bed.

Description of the Related Art

Patients who suffer from conditions such as epilepsy, asthma, chronic heart disease, Alzheimer's, and other conditions with unpredictable outcomes may need to be constantly monitored for timely assistance and safety. Additionally, patients who suffer from conditions that need periodic shifting of their body orientation in order to prevent digression of the condition or to promote healing from the condition may also need to be constantly monitored to ensure that the proper shifts in their body orientation take place.

SUMMARY

In accordance with one embodiment, a computer-implemented method for learning a model to predict movements of a person in bed is provided. The computer-implemented method includes receiving first data from a plurality of first sensors installed in bed, receiving second data from a plurality of second sensors installed on the person, and learning a model to predict the second data based on the first data by assuming a sensing range of motion intensity by the plurality of first sensors is greater than a sensing range of motion intensity by the plurality of second sensors.

In accordance with another embodiment, a non-transitory computer-readable storage medium for learning a model to predict movements of a person in bed is provided. The non-transitory computer-readable storage medium includes a computer-readable program executed on a processor in a data processing system for learning a model to predict movements of a person in bed, wherein the computer-readable program when executed on the processor causes a computer to perform the steps of receiving first data from a plurality of first sensors installed in bed, receiving second data from a plurality of second sensors installed on the person, and learning a model to predict the second data based on the first data by assuming a sensing range of motion intensity by the plurality of first sensors is greater than a sensing range of motion intensity by the plurality of second sensors.

In accordance with yet another embodiment, a system for learning a model to predict movements of a person in bed is provided. The system includes a plurality of first sensors installed in bed for outputting first data, a plurality of second sensors installed on the person for outputting second data, and a learning model for learning to predict the second data based on the first data by assuming a sensing range of motion intensity by the plurality of first sensors is greater than a sensing range of motion intensity by the plurality of second sensors.

Furthermore, embodiments can take the form of a related computer program product, accessible from a computer-usable or computer-readable medium providing program code for use, by or in connection with a computer or any instruction execution system. For the purpose of this description, a computer-usable or computer-readable medium can be any apparatus that may include means for storing, communicating, propagating or transporting the program for use, by or in a connection with the instruction execution system, apparatus, or device.

These and other features and advantages will become apparent from the following detailed description of illustrative embodiments thereof, which is to be read in connection with the accompanying drawings.

BRIEF DESCRIPTION OF THE SEVERAL VIEWS OF THE DRAWINGS

The invention will provide details in the following description of preferred embodiments with reference to the following figures wherein.

Throughout the drawings, same or similar reference numerals represent the same or similar elements.

DETAILED DESCRIPTION

Embodiments in accordance with the present invention provide methods and devices for estimating motion intensity of a person in bed. In a healthcare environment, the quality of sleep of patients is important. The quality of sleep can be inferred by motion intensity (turnover) attributed to the patients. In general, motion intensity can be obtained from sensors attached to a body of the patient. However, these sensors can be intrusive, as they can cause a burden to the patient. In accordance with the present invention, methods and devices provide for additional sensors that are incorporated or embedded or attached to various parts of the bed of the patient for obtaining motion intensity data. In one example, load sensors mounted under the bed (or under the bed legs) can aid in detecting motion intensity in a non-invasive manner. The load sensors mounted under the bed (or under the bed legs) provide data or information that can be employed to estimate motion intensity obtained from the sensors attached to the body of the patient.

Embodiments in accordance with the present invention provide methods and devices for estimating motion intensity obtained by the intrusive sensors from data obtained by the load sensors mounted on various parts of the bed. A learning model is employed to predict movements of a person in bed based on data from bed sensors by assuming a sensing range of the motion intensity by the bed sensor is greater than a sensing range of the motion intensity of the intrusive sensor.

It is to be understood that the present invention will be described in terms of a given illustrative architecture; however, other architectures, structures, substrate materials and process features and steps/blocks can be varied within the scope of the present invention. It should be noted that certain features cannot be shown in all figures for the sake of clarity. This is not intended to be interpreted as a limitation of any particular embodiment, or illustration, or scope of the claims.

Figure 1:
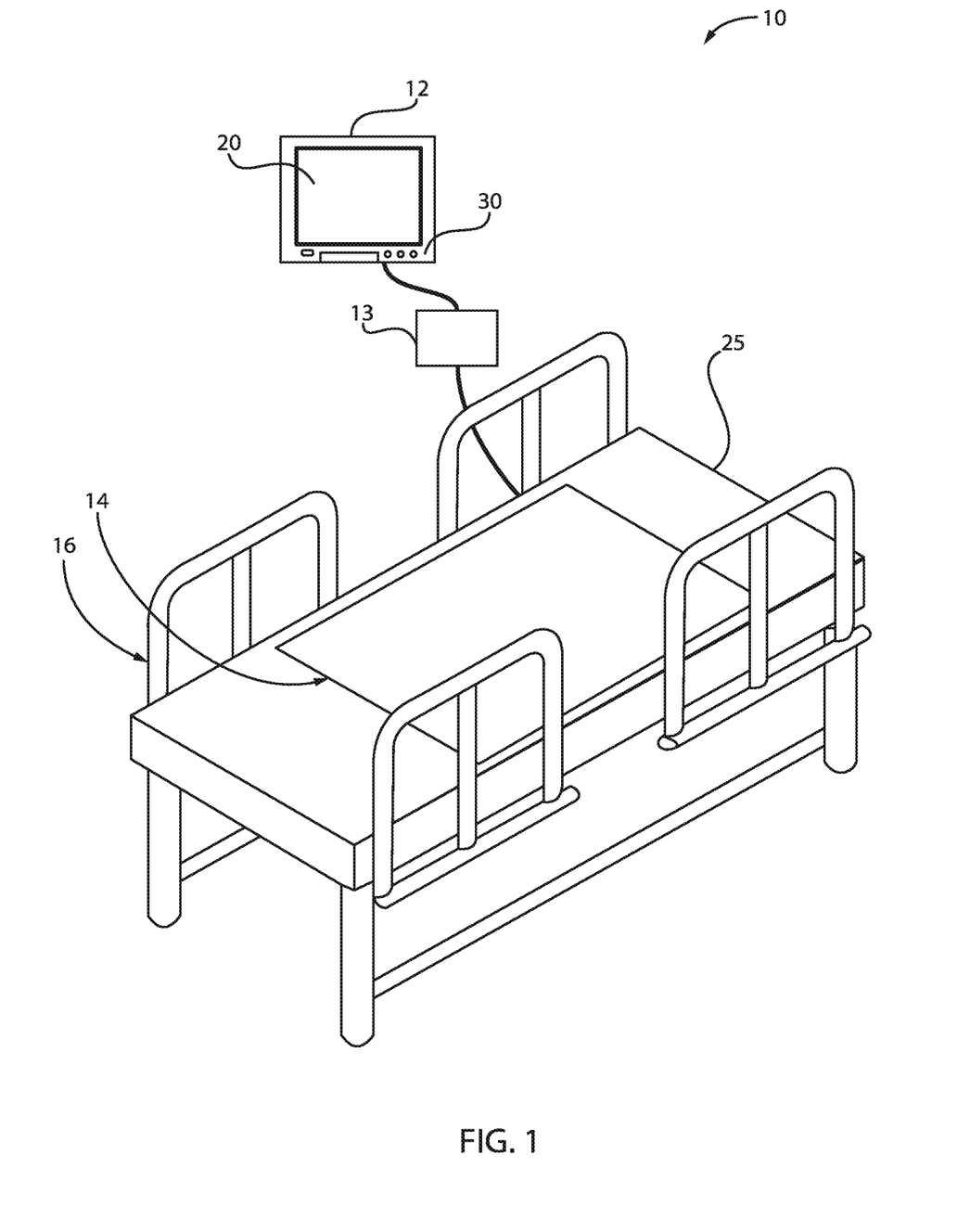
FIG. 1 is a block/flow diagram of an exemplary monitoring system for monitoring movement of a person in bed, in accordance with an embodiment of the present invention.

Referring now to the drawings in which like numerals represent the same or similar elements and initially to FIG. 1, a block/flow diagram of an exemplary monitoring system for monitoring movement of a person in bed is presented, in accordance with an embodiment of the present invention.

As shown in the drawings for purposes of illustration, the invention is embodied in a patient monitoring system 10 having a bedside unit 12 connected to a sensing array 14 placed under the patient in a hospital bed 16. The bedside unit 12 houses a signal processor and an alarm processor to analyze the data received from the sensing array 14 and to activate an alarm when a clinically significant event is occurring. A pre-processor and signal conditioning circuit 13 is further provided to interface the sensing array 14 with the processor in the bedside unit 12.

The bedside unit 12 can be a wall-mounted unit with a display 20 that becomes activated only when an alarm condition is detected or on command by the nurse, by touching a key on the unit 12. Alternatively, the display can be configured to remain on at all times. The bedside unit 12 can be provided with a number of dedicated and soft key buttons and other user controls 30 for entering information, setting up specific items and interfacing with the system. A memory within the bedside unit 12 stores software programs and other information to be used by the processor in analyzing the signals received from the sensing array 14.

While various types of sensor devices can be used, in one embodiment, the sensing array 14 can include a plurality of thin piezoelectric sensing films or other similar sensing technology for sensing a patient's vital signs or other physiological parameters, and a plurality of pressure sensors disposed between the piezoelectric films which produce a pattern of signals indicative of whether a patient is in bed, out of bed, or is actively in the process of exiting the bed or any movements made by the patient while on the bed. Both the piezoelectric films and pressure sensors can be placed in the bed, under the bed, on the legs of the bed, under the legs of the bed, or any other portion or part of the bed without any direct attachment to the patient's body.

The sensing array 14 is shown disposed on top of a mattress coverlet 25 for ease of illustration, but in most cases, it will be advantageous for the sensing array 14 to be attached to the inside of the top surface of the coverlet for invisibility in use, ease of retrofit to existing hospital beds, and to protect the sensing elements and circuits from moisture and provide for added patient safety.

The signal processor within the bedside unit 12 is made up of hardware and software that accepts, buffers and converts the signals from the piezoelectric sensors from analog to digital form for processing to determine a patient's vital signs or other physiological parameters. The vital signs data, such as heart rate and respiration rate, and other physiological parameters derived by the signal processor, can be displayed in real time in numeral and/or graphical form on the display screen 20 of the bedside unit 12, or they can be recorded in memory for subsequent playback and review.

In addition to monitoring the patient's physiological parameters, the software inside the bedside unit 12 can also be programmed to continually observe the state of the various pressure sensors and use logic to determine, from the pattern of sensor states observed, whether the patient is in bed, out of bed, or is attempting to exit the bed, or any movements made by the patient while on the bed.

Figure 2:
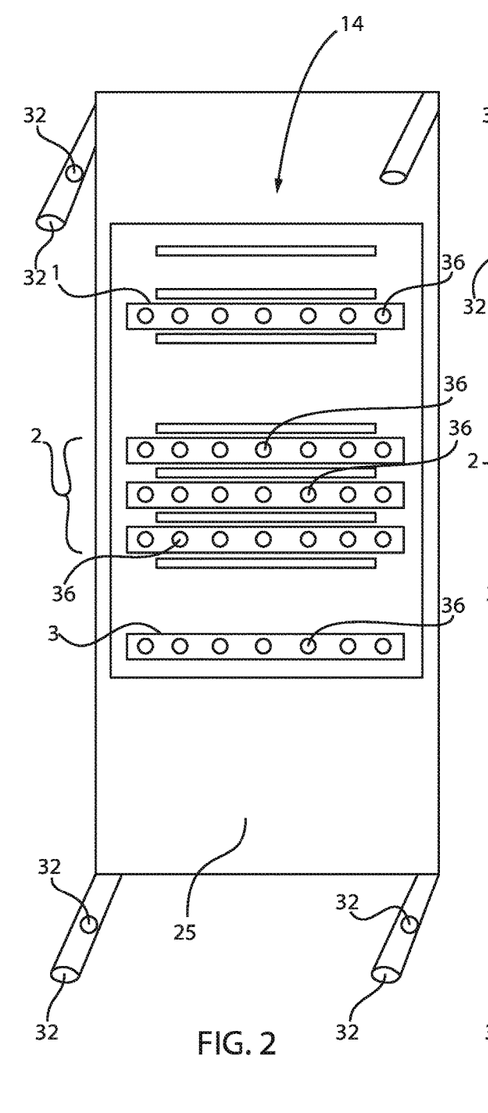
FIG. 2 is a top view of the monitoring system of FIG. 1 where a plurality of first sensors are incorporated into various parts of the bed, in accordance with an embodiment of the present invention.
Figure 3:
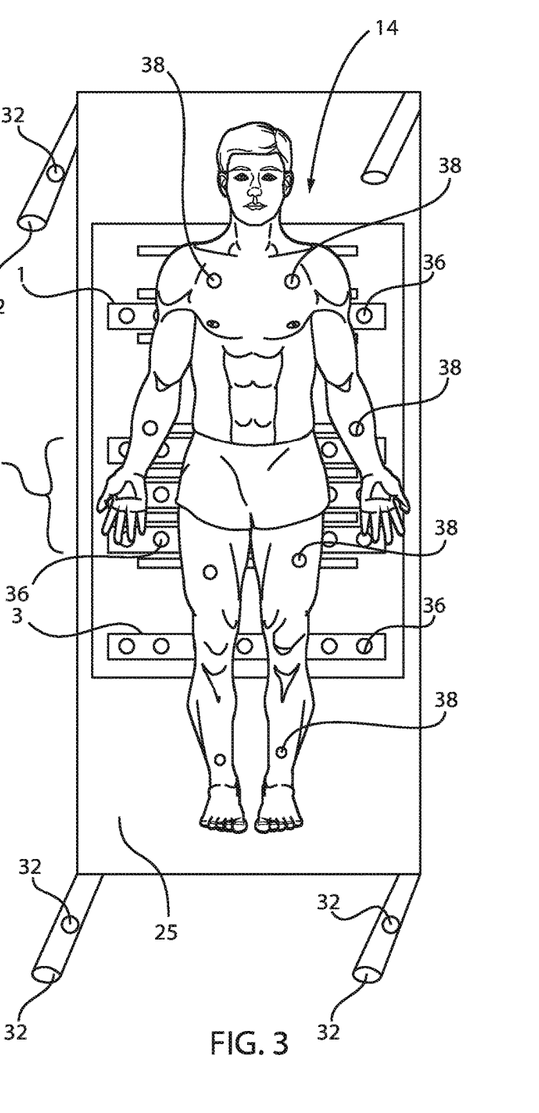
FIG. 3 is a top view of the monitoring system of FIG. 2 where a person is laying on the bed, the patient having a plurality of second sensors attached thereto, in accordance with an embodiment of the present invention.

FIG. 2 is a top view of the monitoring system of FIG. 1 where a plurality of first sensors are incorporated into various parts of the bed, in accordance with an embodiment of the present invention, whereas FIG. 3 is a top view of the monitoring system of FIG. 2 where a person is laying on the bed, the patient having a plurality of second sensors attached thereto, in accordance with an embodiment of the present invention.

The layout of FIGS. 2 and 3 can include a plurality of piezoelectric film strips (not shown) that run laterally across the bed 16 in a pattern that spans most of the patient's body 34 from the shoulders to the thighs. Electrical signals are conducted from each film strip by conductive traces and wires (not shown) through the signal conditioning circuit 13 to the bedside unit 12 for processing to derive the desired vital signs data, as well as patient movement data.

As shown in FIGS. 2 and 3, the sensor array 14 also includes a plurality of pressure sensors 36 for determining in-bed movements by the patient. Various numbers of sensors 36 can be arranged in a pattern to cover the area of the mattress 25 from a patient's torso to legs. Many different kinds of pressure sensors 36 can be used, but round, flat pressure switches, such as membrane switches, can be suitable for hospital bed applications. Those switches 36 can be mounted to the inside of the top surface of the coverlet 25 and electrically connected to the bedside unit 12 in a manner to be described. Software inside the bedside unit 12 is programmed to continually observe the state of these switches to determine whether the patient is in bed, out of bed, or is actively attempting to exit the bed. If desired, sensors of different sensitivity can be used in different areas of the bed. For example, more sensitive sensors 36 can be used in parts of the torso area of the patient's bed.

The sensor array 14 also includes a plurality of pressure sensors 32 incorporated or mounted on the bed legs or positioned under the bed legs in one preferred embodiment. Moreover, the patient 34 can also have a plurality of sensors 38 attached thereon from head to toe. The number of sensors 32, 36, 38 can be determined by the physician based on a number of factors or parameters.

Each sensor 36, 38 in the array 14 can be identified by a unique zone and section designation. In the illustrated embodiment, as best shown in FIGS. 2 and 3, the sensors 36, 38 can be arranged into, e.g., three zones. Each zone is a rectangular strip of sensors 36 extending laterally across the bed 16. One zone (zone 1) is arranged to be located in the torso and, especially near the mid-back region of an adult-sized patient reclining on the bed. A second zone (zone 2) is arranged in the patient's hip area. Another zone (zone 3) is located in the mid-leg area. A gap of some distance is maintained between the head end of the mattress and the mid-back zone 1, the mid-back zone 1 and the hip zone 2, between the mid-leg zone 3 and the hip zone 2, and between the mid-leg zone 3 and the foot end of the mattress, respectively.

In the illustrated embodiment, all the zones 1, 2, 3 are arranged parallel to each other, and each zone includes individual sensors 36 placed at discrete, equally spaced locations across the bed 16 within the zone. In at least one embodiment, the sensors 36 are positioned so as to provide sufficient left-to-right coverage for a standard size mattress. The use of rectangular strips permits side-to-side patient movement, particularly for patient 34 lying on his or her side. The use of multiple zones 1, 2, 3 in the areas described also allows for some degree of up/down patient movement on the bed surface. The gaps between switches (within a zone) provide cost savings by minimizing the size and number of switches employed while not being so large so as to reduce ability to detect patients, especially a small patient lying on his or her side. Additionally, all sensors can run parallel along the left-right axis of bed so as to minimize the amount of material at the articulation point of the bed and to minimize wrinkling and bending of sensors, extending product life as well as minimizing wrinkles which can create localized areas of increased pressure applied to the patient.

It will be appreciated that the number of zones can be increased or decreased from those shown in FIGS. 2 and 3. Thus, for example, an additional zone can be added above zone 1 for greater sensitivity and resolution in the upper torso area of the bed or to better sense the sensors 38 attached to the body of the patient.

Figure 4:
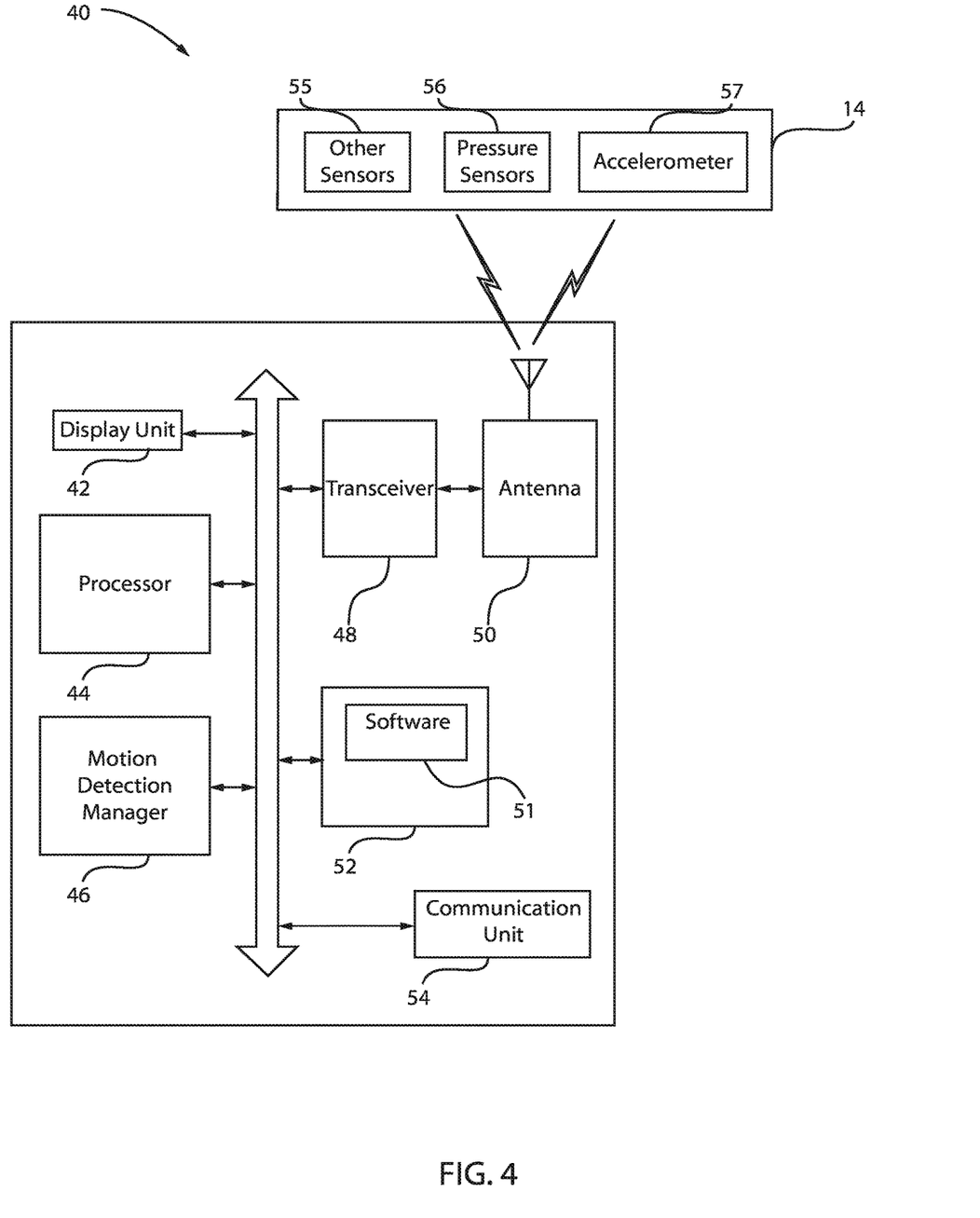
FIG. 4 is a block/flow diagram of an exemplary computing system for monitoring bed movement of a person laying on the bed, in accordance with an embodiment of the present invention.

FIG. 4 is a block/flow diagram of an exemplary computing system for monitoring bed movement of a person laying on the bed, in accordance with an embodiment of the present invention.

System 40 supports patient movement in accordance with various aspects of the present disclosure. System 40 can also include pressure sensors 56, accelerometers 57, and any other types of sensors 55. Pressure sensors 56 can be disposed under a patient that is lying in a medical bed and can be configured to collect pressure data associated with movement of the patient. Pressure sensors 56 can be disposed on various parts of the part, including on the legs of the bed, as well as under the legs of the bed. Accelerometers 57 can be coupled with the patient 34 and can be configured to collect accelerometry data associated with movement of the patient 34. System 40 can be configured to determine the movement of the patient 34 based at least in part on the collected pressure data and the collected accelerometry data.

System 40 can include motion detection manager 46. System 40 can also include memory 52, display unit 42, processor 44, transceiver 48, and antenna 50. Each of these modules can communicate, directly or indirectly, with one another (e.g., via one or more buses) or with external communication units 54. The memory 52 can be in electronic communication with the processor 44 and can include random access memory (RAM) and read only memory (ROM).

The memory 52 can store computer-readable, computer-executable software (e.g., software 51) including instructions that, when executed, cause the processor to perform various functions described herein (e.g., patient movement, etc.). In some cases, the software 51 may not be directly executable by the processor but can cause a computer (e.g., when compiled and executed) to perform functions described herein.

The processor 44 can include an intelligent hardware device, (e.g., a central processing unit (CPU), a microcontroller, an application specific integrated circuit (ASIC), etc.). The transceiver 48 can communicate bi-directionally, via one or more antennas, wired, or wireless links, with one or more networks, as described above. The transceiver 48 can also include a modem to modulate the packets and provide the modulated packets to the antennas for transmission, and to demodulate packets received from the antennas. In some cases, system 40 can include a single antenna 50. However, in some cases the device can have more than one antenna 50, which can be capable of concurrently transmitting or receiving multiple wireless transmissions.

Figure 5:
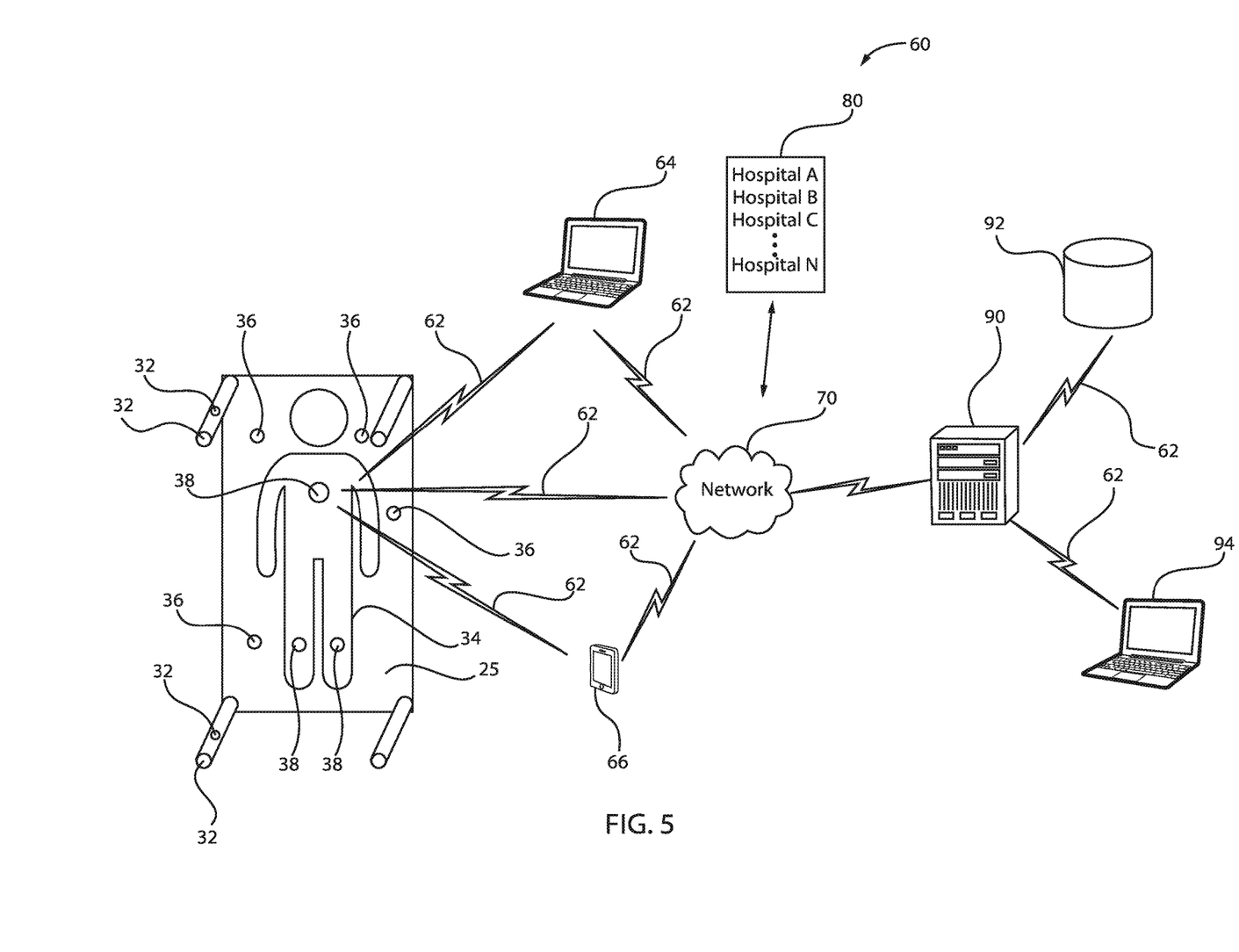
FIG. 5 is a block/flow diagram of an exemplary wireless device that supports bed movement detection, in accordance with an embodiment of the present invention.

FIG. 5 is a block/flow diagram of an exemplary wireless device that supports bed movement detection, in accordance with an embodiment of the present invention.

The wireless patient monitoring system 60 includes a patient 34 wearing, carrying, disposed on, or otherwise coupled with sensor units 32, 36, 38. The patient 34 can be a patient in a hospital, nursing home, home care, or other medical care facility. The sensor units 32, 36, 38 can transmit signals via wireless communications links 62 to local computing devices 64, 66 or to a network 70. In some cases, the sensor units 32, 36, 38 can be used to detect movement of the patient 34. The movement can be indicative of an attempt of the patient 34 to perform some particular activity.

Local computing device 64, 66 can be a wireless device such as a tablet, cellular phone, personal digital assistant (PDA), dedicated receiver or other similar device or a spatially distributed network of devices configured to receive signals from the sensor units 32, 36, 38. Local computing device 64, 66 can be a wireless laptop computer or mobile computer station also configured to receive signals from the sensor units 32, 36, 38. In accordance with various embodiments, a local computing device 64, 66 can be configured to receive data associated with movement of the patient 34. The local computing devices 64, 66 can be in communication with a central station 90 via network 70.

The sensor units 32, 36, 38 can also communicate directly with the central station 90 via the network 70. The central station 90 can be a server or a nurses station located within the hospital or in a remote location. The central station 90 can be in further communication with one or more remote computing devices 94, thus allowing a clinician to remotely monitor the patient 34. The central station 90 can also be in communication with various remote databases 92 where the collected data can be stored.

The sensor unit 32, 36, 38 can include one or more sensors configured to collect a variety of physiological parameters as well as information related to the location and movement of the patient 34. For example, the sensor units 32, 36, 38 can include a pulse oximetry (SpO2) sensor, a heart rate sensor, a blood pressure sensor, a pressure sensor, an electrocardiogram (ECG) sensor, a respiratory rate sensor, a glucose level sensor, a body temperature sensor, an accelerometer, a global positioning sensor, a sensor which triangulates position from multiple local computing devices 64, 66, and any other sensor configured to collect physiological, location, or motion data.

The sensor units 32, 36, 38 can be coupled with the patient 34 in a variety of ways depending on the data being collected. For example, the sensor units 32, 36, 38 can be directly coupled with the patient 34 (e.g., physically connected to the patient's chest, worn around the patient's wrist, or attached to the patient's finger). The sensors 32, 36, 38 can be indirectly coupled with the user so that movement of the patient 34 is detected even though the sensor is not in direct contact with, or physically connected to, the patient 34 (e.g., the sensors 32, 36, 38 can be disposed under the patient 34). The data collected by the sensor units 32, 36, 38 can be wirelessly conveyed to either the local computing devices 64, 66 or to the remote computing device 94 (via the network 70 and central station 90). Data transmission can occur via, for example, frequencies appropriate for a personal area network (such as Bluetooth®, Bluetooth Low Energy® (BLE), or infrared (IR) communications) or local (e.g., wireless local area network (WLAN)) or wide area network (WAN) frequencies such as radio frequencies specified by IEEE standards (e.g., IEEE 802.15.4 standard, IEEE 802.11 standard (Wi-Fi), IEEE 802.16 standard, etc.).

In one implementation, the network 70 can communicate with a plurality of hospitals 80. Each of the hospitals 80 can include a plurality of patients. Each of the plurality of patients can be associated with sensors, e.g., pressure sensors. The movement of each patient of each hospital can be monitored, determined, and collected into a central database. Thus, the training data can be collected to a central location from multiple patients staying at multiple hospitals across multiple locations (counties, states, countries, etc.). Therefore, a predictive training model can be created by assembling information or data from a plurality of patients within the same hospital or from a plurality of different hospitals.

Figure 6:
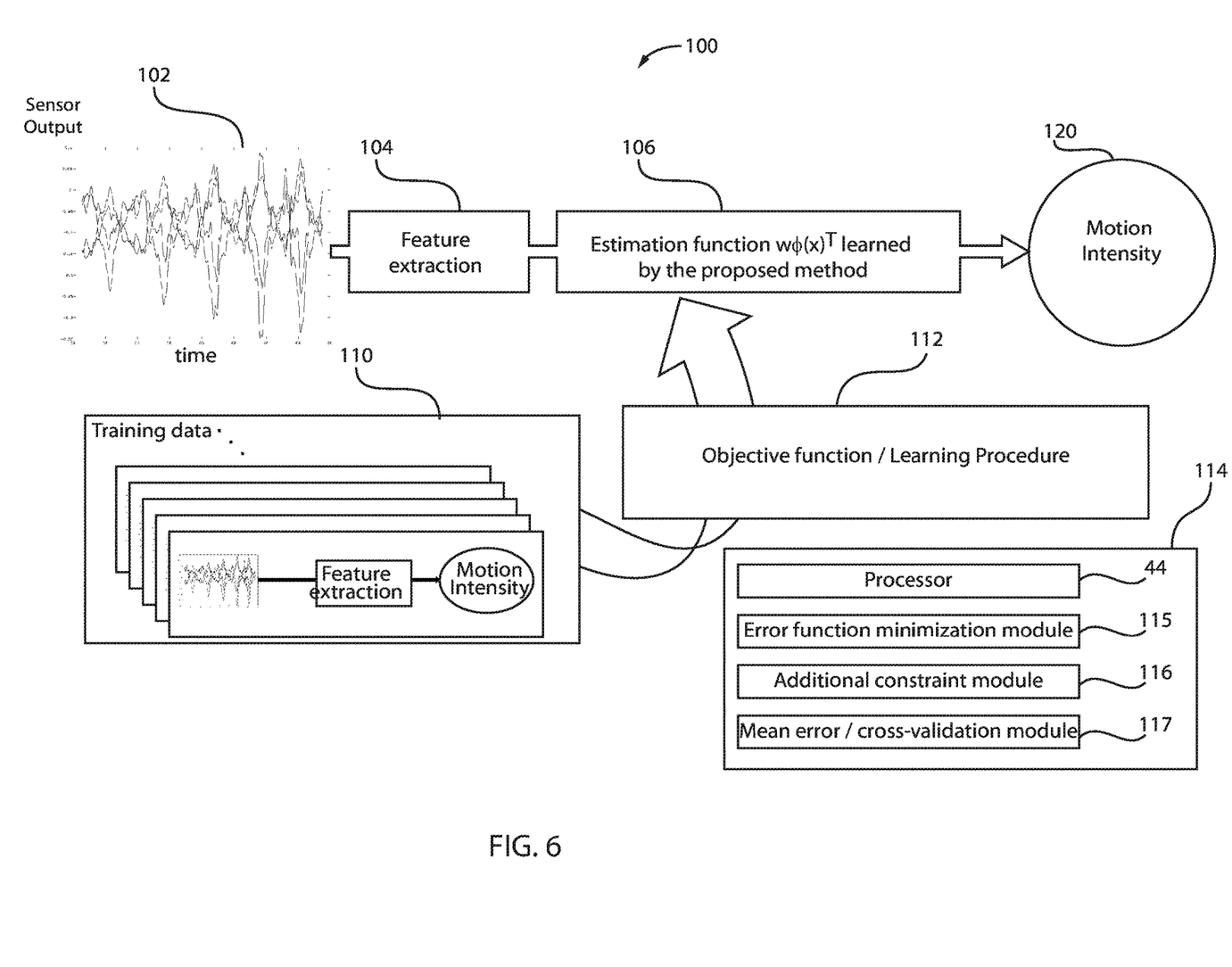
FIG. 6 is a block/flow diagram of an exemplary method for manipulating training data to estimate motion intensity, in accordance with an embodiment of the present invention.

FIG. 6 is a block/flow diagram of an exemplary method for manipulating training data to estimate motion intensity, in accordance with an embodiment of the present invention.

Sensor data, such as pressure sensor data 102 is collected from a plurality of pressure sensors associated with one or more patients from one or more rooms from one or more medical facilities and provided to a feature extraction module 104. The feature extraction module 104 provides feature extraction data that is compared to the training data 110. An estimation function 106 can be learned by employing objective function learning procedures 112. The estimation function 106 can output motion intensity data 120. The objective function learning procedure 112 can be run by different configurations 114. The different configurations 114 can be employing an error function minimization module 115, an additional constraint module 116, and a mean error/cross-validation module 117.

In particular, the motion sensed by the bed sensors and the motion sensed by the intrusive sensors are different. The bed sensor senses not only motion types which can be sensed by the intrusive sensor, but also senses meaningless motion types, such as smoothing and chat. On the other hand, in certain situations the intrusive sensor cannot sense motions from specific local parts of the body, such as the arm, the leg, and/or the head.

As a result, if existing regression models for estimating motion intensity obtained by the intrusive sensors are learnt from the bed sensor data, the model cannot estimate a meaningful motion which can be sensed only by the bed sensors. Since, in the training data, the bed sensor data sequences and the corresponding motion intensity obtained by the intrusive sensor are inconsistent, the learning of the model becomes less efficient. The evaluation criteria are not obvious due to the above situation.

The solution can be to use the following knowledge: (1) that the sensing range of the motion intensity by the bed sensor is greater than the motion intensity by the intrusive sensor, (2) when sleeping, a frequency of the motion is relatively rare, and (3) a frequency of the above inconsistency between the bed sensor and the intrusive sensor is relatively rare.

Based on the knowledge for bed sensor, intrusive sensor, and relationship between them, different objective function and learning procedure configurations can be employed.

Concerning the error function minimization module 115, based on the knowledge (1) above, the error function to be minimized for the task can be used.

For example:

$$\min_w[\Sigma_{\{trainig\ data\}}\max(0, y - w\varphi(x)^T)]$$

where y is the output of the intrusive sensor, x is the feature vector computed from bed sensor output, $\varphi(\ )$ is the basis function, and w is the weights for the feature vector.

This error function is penalized when the output value of the intrusive sensor is higher than the estimation result of motion intensity by the bed sensor.

The model is learnt so that the estimation result of motion intensity by the bed sensor covers over the output of the intrusive sensor.

Concerning the additional constraint module 116, based on the knowledge (2) above, an additional constraint for the task is introduced.

The optimization result based on the error function in the error function minimization module 115 has local optimum, that is, the estimation result is always higher than the maximum value of y in the training data.

The following additional constraint is introduced (when sleeping, the frequency of the motion is relatively rare) to the error function:

$$\min_w[\Sigma_{\{trainig\ data\}}\max(0, y - w\varphi(x)^\textasciitilde T) + \lambda_1 |w\varphi(x)^\textasciitilde T|^2]$$

where $\lambda_1$ is the parameter balancing the effect between the first term and the second term.

Concerning the mean error/cross-validation module 117, based on the knowledge (3) above, the above error function is optimized for obtaining learned w based on the mean error computed by the cross-validation.

By introducing the regularization term and employing an adaptive gradient (AdaGrad) algorithm, a regularized dual averaging (RDA) algorithm, and/or a subgradient-method, the exemplary embodiments optimize the following function for obtaining learned w:

$$\min_w[\Sigma_{\{trainig\ data\}}\max(0, y - w\varphi(x)^\textasciitilde T) + \lambda_1 |w\varphi(x)^\textasciitilde T|^2 + \lambda_2 |w|]$$

where $\lambda_1$ and $\lambda_2$ are optimized based on the mean error computed by the cross-validation.

The new data can be predicted as $w\varphi(x)^T$ using learned w.

In one example, the learning can be employed by the training/learning system 112 and can be implemented by, e.g., deep machine learning methods. The exemplary embodiments of the present invention can be directed generally to deep machine learning methods and apparatuses. Some implementations are directed to training a deep neural network, such as a convolutional neural network (also referred to herein as a "CNN"), to predict patient movement in a bed. In some implementations of the training/learning system 112, a method can be provided that includes, e.g., identifying a plurality of training examples generated based on sensor output from the pressure sensors mounted to the bed.

The learning/training system 112 can have the function of extracting, e.g., a useful rule, a knowledge representation, and a determination criterion by analysis from a set of data input to the learning/training system 112, outputting determination results, and learning knowledge (machine learning). It is noted that a variety of machine learning techniques are available, which can be roughly classified into, e.g., "supervised learning," "unsupervised learning," and "reinforcement learning." To implement these techniques, "deep learning" can be employed, as discussed above.

Variations of the method and/or system can be implemented in characterizing and/or improving sleep-related conditions including one or more of: jet lag, narcolepsy, night terror, sleep walking, sleep apnea (e.g., obstructive sleep apnea, central sleep apnea, complex sleep apnea syndrome, etc.), restless legs syndrome, bruxism, delayed sleep phase disorder, hypopnea syndrome, insomnia, Kleine-Levin syndrome, nocturia, parasomnias, periodic limb movement disorder, rapid eye movement disorder, shift work sleep disorder, sleep paralysis, somniphobia, catathrenia, idiopathic hypersomnia, conditions associated with sleep-related conditions (e.g., alcoholism, mood disorders, anxiety disorders, panic, psychosis, etc.), and/or any other suitable sleep-related conditions. In relation to depression and/or anxiety (and/or other mental health-related disorders), which can be combined with sleep-related disorders, applications of the method can be adapted to provide therapeutic interventions to improve sleep behavior in order to improve outcomes and health in relation to states of depression and/or anxiety of the user.

Additionally or alternatively, one or more instances of the method and/or processes described herein can be performed asynchronously (e.g., sequentially), concurrently (e.g., in parallel; concurrently on different threads for parallel computing to improve system processing ability for characterizing and/or promoting therapeutic interventions for sleep-related conditions; etc.), in temporal relation to a trigger event, and/or in any other suitable order at any suitable time and frequency by and/or using one or more instances of the system, elements, and/or entities described herein. However, the method and/or system can be configured in any suitable manner.

The technology can overcome several challenges faced by conventional approaches in characterizing and/or promoting therapeutic interventions for sleep-related conditions. First, conventional approaches to characterizing sleep-related conditions can require users to visit a care provider (e.g., physicians, sleep specialists, sleep consultants, etc.) and/or sleep testing laboratories (e.g., which can require overnight sleep experiments to characterize a sleep-related condition, etc.). Second, conventional sleep characterization approaches can be inaccurate, such as due to failing to account for unique user behaviors (e.g., digital communication behaviors, mobility behaviors, etc.), for natural conditions (e.g., where conventional approaches can be limited to sleep characterization in unnatural settings), data collection limitations (e.g., quantity of users from which data is collected; amount of data collected per user; rate of data collection; etc.). Third, conventional sleep care plans and/or therapeutic interventions for improving sleep-related conditions can be inconvenient, invasive, and/or impersonalized to the user and their user behaviors.

In one exemplary embodiment, the technology can confer improvements in computer-related technology (e.g., digital communication behavior analytics, computationally-based sleep characterization, digital administration of therapeutic interventions for sleep-related conditions, artificial intelligence, etc.) by facilitating computer performance of functions not previously performable. For example, the technology can improve sleep characterization and treatment through leveraging passively collected digital communication data (e.g., text messaging features, phone calling features) and/or supplementary data (e.g., mobility behavior data extracted from GPS sensors of mobile devices) that would not exist but for advances in mobile devices (e.g., smartphones) and associated digital communication protocols (e.g., WiFi-based phone calling). As such, the technology can, in examples, unobtrusively evaluate and treat sleep-related conditions by continuously gathering a plethora of data that can be used to personalize sleep parameter characterizations and sleep care plans for a user and associated changes in behavior over time, while requiring a minimal or otherwise reduced amount of effort by a patient. In a specific example, the technology can enable data collection for users in their natural sleep setting (e.g., their home), which can enables extraction of insights into differences in sleep patterns due to natural conditions (e.g., sleeping in the same bed with a partner, interactions with family, daily routines, digital activity over time, etc.), rather than, for example, laboratory conditions (e.g., which can also be monitored by the technology).

In another exemplary embodiment, the technology can confer improvements in computer-related technology through an inventive distribution of functionality across a network including a sleep characterization system (e.g., a remote computing system receiving and analyzing digital communication data across a plurality of users), a plurality of mobile devices (e.g., associated with users possessing a diversity of sleep-related conditions and behaviors), a treatment system (e.g., operable to promote one or more therapeutic interventions to the users, such as at the plurality of mobile devices), and/or other suitable components. For example, the sleep characterization system can include functionality of analyzing digital communication data previously unused for sleep characterization, such as digital communication data derived from a population of users (e.g., patients) and usable for providing insight into connections between a user's digital communication behavior and sleep-related conditions. Such data and insights can subsequently be used to provide, evaluate, and/or subsequently update therapeutic interventions for each user in a tailored, customizable, and dynamically modifiable sleep care plan, the personalization of which can improve user engagement with the sleep care plan. As such, the technology can provide a centralized, full-stack approach to digitally monitoring the physiological and psychological sleep-related health of a patient, leading to improved efficiency of care delivery, cost savings, and care delivery scalability.

In another exemplary embodiment, the technology can confer improvements in computer-related technology through computer-implemented rules (e.g., feature engineering rules; therapeutic intervention rules; etc.). The increasing prevalence of user digital communication across a plurality of communication protocols can translate into a plethora of digital communication data, giving rise to questions of how to process and analyze the vast array of data, such as for generating actionable sleep-related insights. However, the technology can address such challenges by, for example, applying feature engineering rules in generating features (e.g., digital communication-mobility behavior features) operable to improve processing speed and/or accuracy of sleep characterization and/or treatment (e.g., to enable real-time sleep characterization and/or real-time provision of therapeutic interventions).

In another exemplary embodiment, the technology can improve the technical fields of at least digital communication, computational modeling of user behavior and/or sleep-related conditions, digital medicine, and/or other relevant fields. The technology can continuously collect and employ specialized datasets unique to internet-enabled, non-generalized mobile devices in order to characterize and/or treat sleep-related conditions. Further, the technology can take advantage of such datasets to better improve the understanding of correlations between patient digital communication behavior, sleep-related conditions, and appropriate therapeutic interventions.

In another exemplary embodiment, the technology can transform entities (e.g., mobile devices, treatment system including medical devices, users, etc.) into different states or things. For example, the technology can automatically initiate provision of therapeutic interventions to the user, such as by activating and/or controlling one or more treatment systems (e.g., supplementary sleep-related devices, mobile communication devices; etc.) to promote the therapeutic interventions. In a specific example, the technology can activate an application executing on a smart phone in automatically providing a sleep-related notification (e.g., recommending that the user minimizes mobile device usage, etc.) in response to sleep-related threshold conditions. In another example, the technology can determine therapeutic interventions to promote to a patient to modify user sleep behaviors in improving sleep-related conditions of the patient, thereby transforming the sleep-related condition and the health of the patient.

In another exemplary embodiment, the technology can provide technical solutions rooted in computer technology (e.g., utilizing computational models for extracting sleep-related parameters based on a user's unique behaviors; dynamically generating and modifying digital sleep care plans including digitally promoted therapeutic interventions, such as sleep-related notifications including hyperlinks to sleep-related content; modifying visually perceptible elements associated with therapeutic interventions to improve, for example, display of the sleep-related notifications in accordance with treating sleep-related conditions; etc.) to overcome issues specifically arising with computer technology (e.g., negative correlations between sleep quality and computer technology usage; modifying elements associated with user interfaces of computer technology to improve sleep-related conditions, such as through modifying display of content).

In another exemplary embodiment, the technology can leverage specialized computing devices (e.g., mobile devices with mobility-related sensors, physical activity monitoring capabilities, digital communication behavior-monitoring capabilities, sleep-related sensors, ambient environment sensors, supplementary sleep-related devices) in sleep characterization and/or treatment. The technology can, however, provide any other suitable benefit(s) in the context of using non-generalized computer systems for characterizing and/or promoting therapeutic interventions for sleep-related conditions.

In some variations, the exemplary systems and methods can include collecting sleep-related parameters associated with sleep-related conditions, such as from electronic health records, sensors of mobile devices and/or supplementary sleep-related devices, user inputs (e.g., entries by the user at the mobile device), and/or other suitable sources. Sleep-related parameters can include one or more of: electroencephalogram (EEG) data, electrooculogram (EOG) data, electromyogram (EMG) data, electrocardiogram (ECG) data, airflow data (e.g., nasal airflow, oral airflow, measured by pressure transducers, thermocouples, etc.), pulse oximetry data, sound probes (e.g., to measure snoring), polysomnography data, family conditions, genetic data, microbiome data, and/or any other sleep-related data.

In some variations, the exemplary systems and methods can receive a survey dataset (e.g., included in a supplementary dataset) including responses, to at least one of a set of sleep-assessment surveys, associated with a set of time points of the time period, from the user. The systems and methods can function to provide survey data associated with a specific time point, time period (e.g., sleep session), and/or other suitable time unit in the life of the user and/or associated users (e.g., a partner sleeping in the same bed with a user; a parent with the same sleeping schedule as their child; etc.). The systems and methods can additionally or alternatively be employed to aggregate survey data from the user over time, in order to generate a personalized model of the user's behavior from self-reported data. The systems and methods can additionally or alternatively be employed to aggregate survey data from a population of users, in order to generate a population model of behavior for a population of users. As such, personalized and/or population-wide models can be used to inform assessments of sleep for each of a population of users (e.g., in terms of estimating sleep-related parameters for a user). The survey dataset can include interview and/or self-reported information from the user. Furthermore, the survey dataset can include quantitative data, but can additionally or alternatively include qualitative data pertaining to a sleep-related condition of the user corresponding to at least a subset of the set of time points.

In some variations of the exemplary systems and methods, the survey dataset can include responses to surveys configured to assess or validate values of one or more sleep-related parameters intended to be determined. While the survey(s) can be provided such that the user is prompted to provide quantitative answers, the survey(s) can additionally or alternatively be provided such that qualitative information provided by the user is transformed into quantitative data according to a response-scoring algorithm. In examples, the set of sleep-assessment surveys can include surveys derived from one or more of: a behavioral risk factor surveillance system questionnaire, a youth risk behavior survey, a national health interview survey, and any other suitable sleep survey. However, the set of surveys can include any other suitable surveys or adaptations thereof. As such, the survey dataset can include quantitative scores of the user for one or more subsets of surveys for each of the set of time points (or a subset of the set of time points).

In some variations of the exemplary systems and methods, the survey dataset can include responses (e.g., weekly responses for a period of n months) to surveys configured to assess sleep patterns in terms of one or more of: self-assessed sleep times, self-assessed waking times, self-assessed sleep quantity (e.g., sleep duration), self-assessed sleep quality (e.g., amount of non-rapid eye movement sleep; amount of rapid eye movement sleep; light sleep; deep sleep; etc.), self-assessed difficulty in falling asleep, and self-assessed daytime drowsiness, assessments from associated users (e.g., guardians, partners, etc.), sleep-related symptoms (e.g., energy levels; headaches; psychological conditions such as depression; swelling; nocturnal urination; gasping; choking; coughing; reflux; irregular breathing; etc.), sleep-related risk factors (e.g., demographics, weight, digital communication behaviors, mobility behaviors such as physical activity, smoking, family history, etc.), and/or other suitable sleep-related parameters.

In some variations of the exemplary systems and methods, determining sleep-related parameters can be performed with a sleep characterization model including any one or more of: probabilistic properties, heuristic properties, deterministic properties, and/or any other suitable properties. In a variation, the sleep characterization model can include weights assigned to different sleep-related features and/or types of sleep-related data. For example, in determining a value for sleep quality, the frequency of text messages during a sleep session can be weighted more heavily than the length of the text messages. In another variation, applying a sleep characterization model can include applying one or more machine learning sleep characterization models employing one or more machine learning approaches.

In a specific example, a training sample can correspond to a single sleep session for a user. The training sample can include digital communication features (e.g., extracted from log of use datasets, etc.), mobility features (e.g., extracted from motion datasets, etc.), and/or other suitable features (e.g., where the feature values are vectorized and/or otherwise processed) and a corresponding label (e.g., a sleep-related parameter value, as determined based on survey datasets including survey responses; biometric sensor measurements taken during the sleep session; and/or any other suitable data). However, applying weights and/or a machine learning sleep characterization models can be performed in any suitable manner.

Figure 7:
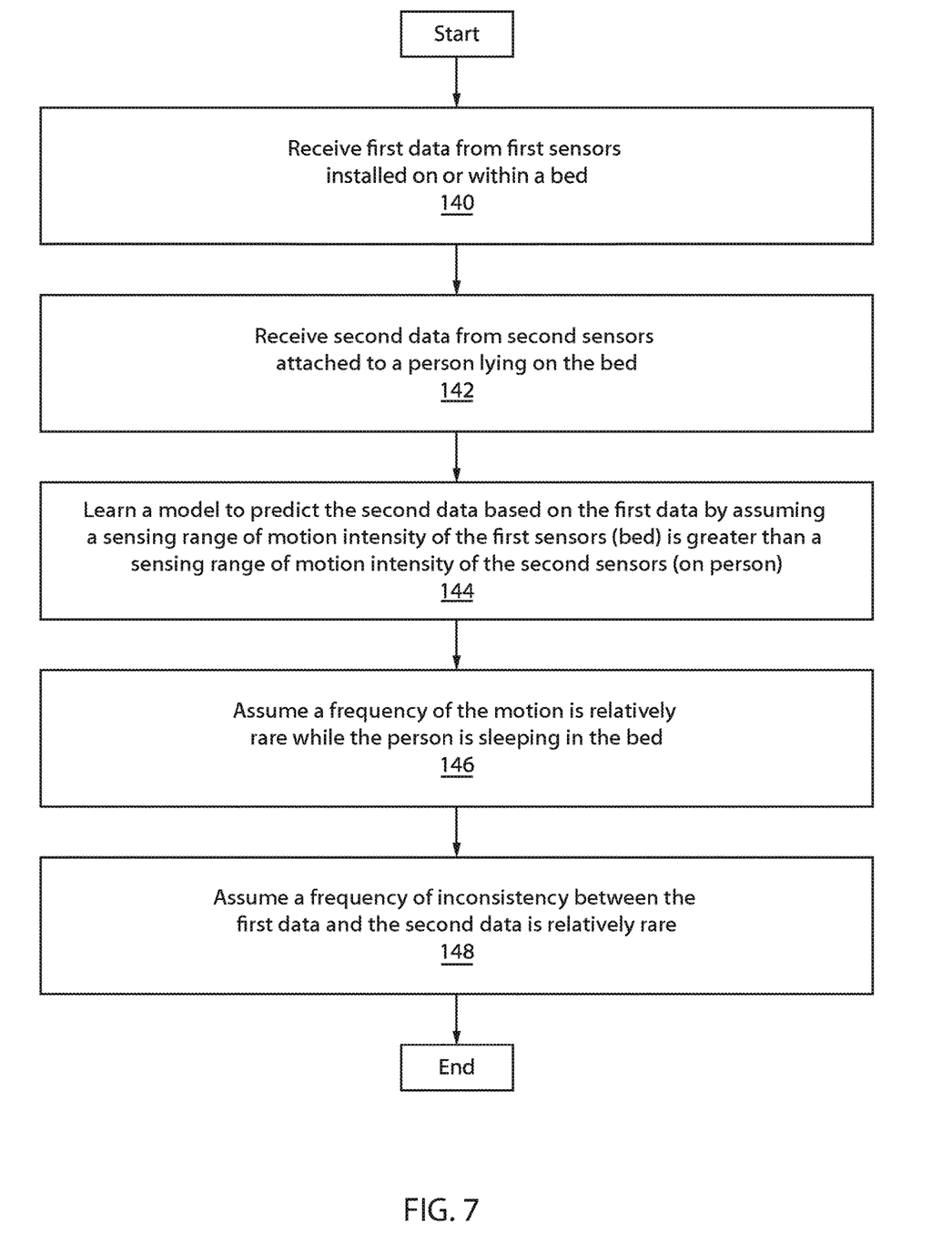
FIG. 7 is a block/flow diagram of an exemplary method for estimating motion intensity of a person in bed, in accordance with an embodiment of the present invention.

FIG. 7 is a block/flow diagram of an exemplary method for estimating motion intensity of a person in bed, in accordance with an embodiment of the present invention.

At block 140, receive first data from first sensors installed on or within a bed. The first sensors can be installed under the legs of the bed.

At block 142, receive second data from second sensors attached to a person lying on the bed. The second sensors can be attached on various portions of the body of the patient.

At block 144, learn a model to predict the second data based on the first data by assuming a sensing range of motion intensity of the first sensors (bed) is greater than a sensing range of motion intensity of the second sensors (on person).

At block 146, assume a frequency of the motion is relatively rare while the person is sleeping in the bed. This is an additional constraint that can be added to the training model.

At block 148, assume a frequency of inconsistency between the first data and the second data is relatively rare.

Figure 8:
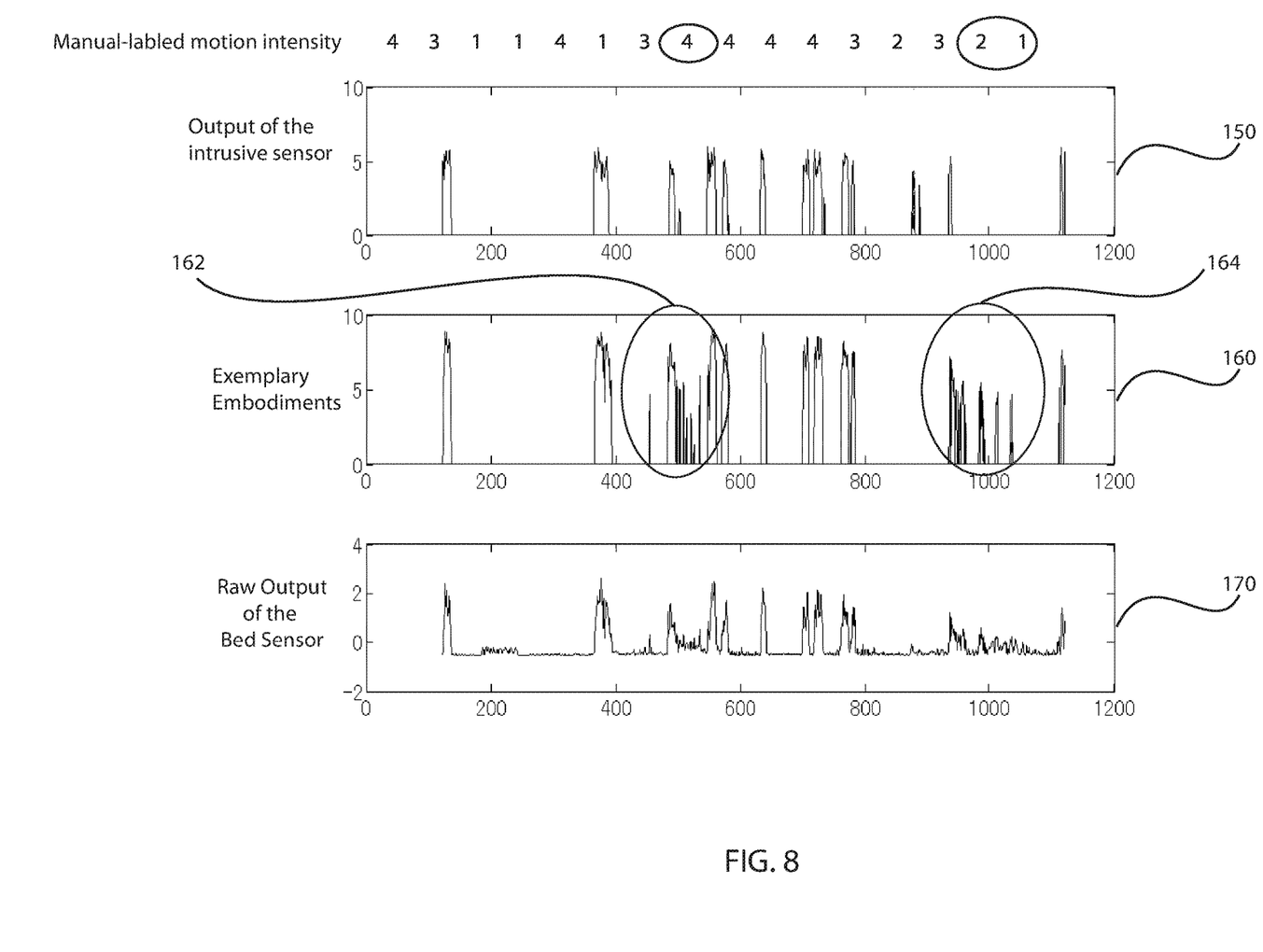
FIG. 8 illustrates exemplary graphs estimating motion intensity of a person in bed, in accordance with an embodiment of the present invention.

FIG. 8 illustrates exemplary graphs estimating motion intensity of a person in bed, in accordance with an embodiment of the present invention.

Graph 150 depicts an output of the intrusive sensor, graph 170 depicts an output of the bed sensor, and graph 160 depicts an output created by the exemplary embodiments of the present invention employing training data. FIG. 8 depicts a comparison between output of the intrusive sensor, the proposed method, and raw output of the bed sensor. The proposed method covers the most of motions sensed by the intrusive sensor and can sense additional motions 162, 164 which cannot be sensed by the intrusive sensor. For instance motions 162, 164 are not sensed accurately by the intrusive sensor (see graph 150) and by the bed sensor (see graph 170).

The descriptions of the various embodiments of the present invention have been presented for purposes of illustration, but are not intended to be exhaustive or limited to the embodiments described. Many modifications and variations will be apparent to those of ordinary skills in the art without departing from the scope and spirit of the described embodiments. The terminology used herein was chosen to best explain the one or more embodiments, the practical application or technical improvement over technologies found in the marketplace, or to enable others of ordinary skills in the art to understand the embodiments described herein.

The present invention can be a system, a method, and/or a computer program product. The computer program product can include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can include copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions can be provided to at least one processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks or modules. These computer readable program instructions can also be stored in a computer readable storage medium that can direct a computer, a programmable data processing apparatus, and/or other devices to function in a particular manner, such that the computer readable storage medium having instructions stored therein includes an article of manufacture including instructions which implement aspects of the function/act specified in the flowchart and/or block diagram block or blocks or modules.

The computer readable program instructions can also be loaded onto a computer, other programmable data processing apparatus, or other device to cause a series of operational blocks/steps to be performed on the computer, other programmable apparatus or other device to produce a computer implemented process, such that the instructions which execute on the computer, other programmable apparatus, or other device implement the functions/acts specified in the flowchart and/or block diagram block or blocks or modules.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which includes one or more executable instructions for implementing the specified logical function(s). In some alternative implementations, the functions noted in the blocks can occur out of the order noted in the figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This can be extended, as readily apparent by one of ordinary skill in this and related arts, for as many items listed.

Having described preferred embodiments of a system and method for employing an estimation model for motion intensity of a patient in bed (which are intended to be illustrative and not limiting), it is noted that modifications and variations can be made by persons skilled in the art in light of the above teachings. It is therefore to be understood that changes may be made in the particular embodiments described which are within the scope of the invention as outlined by the appended claims. Having thus described aspects of the invention, with the details and particularity required by the patent laws, what is claimed and desired protected by Letters Patent is set forth in the appended claims.

The invention claimed is:

1. A computer-implemented method for learning a model to predict movements of a person in a bed, the method comprising:

receiving first data from a plurality of first sensors installed on the bed;

receiving second data from a plurality of second sensors installed on the person; and learning, via a machine learning procedure in a central computer database implemented by deep neural networks employing a feature extraction module and motion intensity training data, an estimation function by employing an objective function, modified by the motion intensity training data, to output an adjusted motion intensity data of the person to predict the second data based on the first data by assuming a first sensing range of a first motion intensity by the plurality of first sensors is greater than a second sensing range of a second motion intensity of the person by the plurality of second sensors; and assuming a frequency of motion is relatively rare while the person is sleeping to improve the objective function and to minimize an error function, wherein the error function is given as:

$$\min_{w}[\Sigma_{[\text{trainig data}]}\max(0, y-w\phi(x)^T)]$$

where y is an output of a second sensor of the plurality of second sensors, x is a feature vector computed from output of a first sensor of the plurality of first sensors, $\phi(\ )$ is a basis function, and w is weights for the feature vector; and wherein the error function is penalized when a second motion intensity output value of the second motion intensity of the plurality of second sensors is higher than a result of a first motion intensity output value of the first motion intensity of the plurality of first sensors.

2. The method of claim 1, further comprising collecting the motion intensity training data from a plurality of patients staving at a plurality of medical facilities located across a plurality of geographical locations.

3. The method of claim 1, further comprising assuming a frequency of an inconsistency between the plurality of first sensors and the plurality of second sensors is relatively rare.

4. The method of claim 1, wherein the machine learning procedure of the central computer database involves employing an additional constraint to the error function for a task.

5. The method of claim 1, wherein the machine learning procedure of the central computer database involves optimizing the error function based on a mean error computed by cross-validation.

6. A non-transitory computer-readable storage medium comprising a computer-readable program executed on a processor in a data processing system for learning a model to predict movements of a person in a bed, wherein the computer-readable program when executed on the processor causes a computer to perform steps of:

receiving first data from a plurality of first sensors installed on the bed;

receiving second data from a plurality of second sensors installed on the person; and learning, via a machine learning procedure in a central computer database implemented by deep neural networks employing a feature extraction module and motion intensity training data, an estimation function by employing an objective function, modified by the motion intensity training data, to output an adjusted motion intensity data of the person to predict the second data based on the first data by assuming a first sensing range of a first motion intensity by the plurality of first sensors is greater than a second sensing range of a second motion intensity of the person by the plurality of second sensors; and assuming a frequency of motion is relatively rare while the person is sleeping to improve the objective function and to minimize an error function, wherein the error function is given as:

$$\min_{w} [\Sigma_{[trainig\ data]} \max(0, y - w \cdot \phi(x)^T)]$$

where y is an output of a second sensor of the plurality of second sensors, x is a feature vector computed from output of a first sensor of the plurality of first sensors, $\phi()$ is a basis function, and w is weights for the feature vector; and wherein the error function is penalized when a second motion intensity output value of the second motion intensity of the plurality of second sensors is higher than a result of a first motion intensity output value of the first motion intensity of the plurality of first sensors.

7. The non-transitory computer-readable storage medium of claim 6, wherein the motion intensity training data is collected from a plurality of patients staving at a plurality of medical facilities located across a plurality of geographical locations.

8. The non-transitory computer-readable storage medium of claim 6, wherein a frequency of an inconsistency between the plurality of first sensors and the plurality of second sensors is assumed to be relatively rare.

9. The non-transitory computer-readable storage medium of claim 6, wherein the learning procedure of the central computer database involves employing an additional constraint to the error function for a task.

10. The non-transitory computer-readable storage medium of claim 6, wherein the learning procedure of the central computer database involves optimizing the error function based on a mean error computed by cross-validation.

11. A system for learning a model to predict movements of a person in a bed, the system comprising:

a plurality of first sensors installed on the bed for outputting first data;

a plurality of second sensors installed on the person for outputting second data; and an estimation function learnt via a machine learning procedure in a central computer database implemented by deep neural networks employing a feature extraction module and motion intensity training data, by employing an objective function, modified by the motion intensity training data, to output an adjusted motion intensity data of the person for learning to predict the second data based on the first data by assuming a first sensing range of a first motion intensity by the plurality of first sensors is greater than a second sensing range of a second motion intensity of the person by the plurality of second sensors, wherein a frequency of motion is assumed to be relatively rare while the person is sleeping to improve the objective function and to minimize an error function, wherein the error function is given as:

$$\min_{w} [\Sigma_{[trainig\ data]} \max(0, y - w \cdot \phi(x)^T)]$$

where y is an output of a second sensor of the plurality of second sensors, x is a feature vector computed from output of a first sensor of the plurality of first sensors, $\phi()$ is a basis function, and w is weights for the feature vector; and wherein the error function is penalized when a second motion intensity output value of the second motion intensity of the plurality of second sensors is higher than a result of a first motion intensity output value of the first motion intensity of the plurality of first sensors.

12. The system of claim 11, wherein a plurality of patients staving at a plurality of medical facilities located across a plurality of geographical locations.

13. The system of claim 11, wherein a frequency of an inconsistency between the plurality of first sensors and the plurality of second sensors is assumed to be relatively rare.

14. The system of claim 11, wherein the machine learning procedure of the central computer database involves employing an additional constraint to the error function for the task.

* * * * *